(12) United States Patent
Lee et al.

(10) Patent No.: US 8,835,624 B1
(45) Date of Patent: Sep. 16, 2014

(54) INFLUENZA A H1N1 SUBTYPE-SPECIFIC APTAMER AND APPLICATIONS THEREOF

(71) Applicant: National Tsing Hua University, Hsinchu (TW)

(72) Inventors: Gwo-Bin Lee, Hsinchu (TW); Tong-Minn Liou, Hsinchu (TW); Chih-Hung Wang, Hsinchu (TW); Hsien-Chih Lai, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 14/185,196

(22) Filed: Feb. 20, 2014

(30) Foreign Application Priority Data

Oct. 23, 2013 (TW) .............................. 102138334 A

(51) Int. Cl.
| | | |
|---|---|---|
| *C07H 21/04* | (2006.01) | |
| *C12Q 1/68* | (2006.01) | |
| *C12N 5/00* | (2006.01) | |
| *C12N 15/00* | (2006.01) | |

(52) U.S. Cl.
USPC .......... 536/24.5; 435/6.1; 435/91.1; 435/325; 435/375

(58) Field of Classification Search
USPC .................. 536/24.5; 435/6.1, 91.1, 325, 375
See application file for complete search history.

(56) References Cited

U.S. PATENT DOCUMENTS

| 8,541,561 B2 | 9/2013 | Ban et al. |
| 8,552,166 B2 | 10/2013 | Tanner et al. |
| 8,569,252 B2 | 10/2013 | Lee et al. |
| 8,624,008 B2 | 1/2014 | Lee et al. |

OTHER PUBLICATIONS

Lai et al. (Lab Chip. 2014 vol. 14, pp. 2002-2013).*

* cited by examiner

*Primary Examiner* — Terra Cotta Gibbs
(74) *Attorney, Agent, or Firm* — WPAT, P.C.; Anthony King; Kay Yang

(57) ABSTRACT

The present invention provides an Influenza A H1N1 subtype-specific aptamer. The aptamer was selected in vitro using SELEX and a microfluidic chip system. The aptamer is stable, establishing sensitivity about 100 times higher than antibody and high specificity to Influenza A H1N1 subtype. Thus, the aptamer can be effective in detection of H1N1 influenza virus.

10 Claims, 6 Drawing Sheets

US 8,835,624 B1

INFLUENZA A H1N1 SUBTYPE-SPECIFIC APTAMER AND APPLICATIONS THEREOF

CROSS-REFERENCES TO RELATED APPLICATIONS

This application claims priority to Taiwan Patent Application No. 102138334 filed on 23 Oct. 2013. All disclosure of which is incorporated herein by reference in its entirety.

BACKGROUND OF THE INVENTION

1. Field of the Invention

The present invention is related to an Influenza A H1N1 subtype-specific aptamer and applications thereof.

2. The Prior Arts

Influenza, or sometimes abbreviated as flu, is an acute respiratory infection caused by influenza viruses. Influenza viruses can spread through aerial and contact infection, therefore, by the advance in transportation and the increase in travel, business, and social interactions, cyclical pandemics occurs throughout the globe, for instance the 1918 Spanish flu and the 1968 Hong Kong flu. Symptoms of influenza include running nose, sore throat, cough, as well as fever, headache, muscle ache, fatigue, etc. Symptoms of influenza are acute and would usually lead to complications, thus, for groups such as the elderly, children, and patients with immunodeficiency, influenza is likely to result in more server symptoms, for example, pneumonitis or cardiorespiratory failure, and even death.

Influenza viruses can be categorized into 3 types: type A, B and C, wherein the type A influenza virus is further subcategorized into many subtypes such as H1N1, H3N2, and H7N9, according to the two types of glycoprotein on the envelope, namely Hemagglutinin (H) and Neuraminidase (N). The threat of influenza lies in its rapid breakout, widespread infection and the possibility of causing sever complications; particularly, type A influenza is the most likely to cause regional epidemic or worldwide pandemic among all other influenzas. Besides, the type A influenza virus is able to cross-infect and recombine between different species, for example, human, swine, and bird, which increases the difficulties of treatment and prevention.

Therefore, early diagnosis and prevention of influenza are vital. The methods of detection for influenza virus infections commonly used nowadays include viral culture, viral nucleic acid detection, serology testing, and rapid influenza diagnostic test. These methods are usually time-consuming with low sensitivity/specificity and require large amount of sample or expensive reagents. Although, rapid influenza diagnostic test is able to obtain result in a short time in a simple manner without the use of special equipment and is able to be performed in clinic or ward, its low sensitivity is likely to cause false negative results and is unable to accurately distinguish the type and subtype of the influenza viruses detected. On the other hand, antibodies with specificity for influenza viruses are often used clinically for detection of influenza virus. Although those antibodies have specificity to influenza viruses, the antibodies themselves are very sensitive to conditions of the surrounding environment such as temperature and moisture, thus, are easy to lose activity and cause inconvenience when transport, store, or use. Furthermore, since antibodies are prepared in batch, activity of antibody is not identical among batches, while errors are likely to occur when operating antibodies due to manual mistakes or effects of the environment of the operation.

Prevention and accurate diagnosis are critical in terms of public health and disease control. Furthermore, accurate diagnosis is the foundation of effective treatment. However, currently the market still lacks an accurate, cost-effective, easy-to-store, and highly efficient method for influenza virus detection.

SUMMARY OF THE INVENTION

As a result, the present invention provides an aptamer comprising (i) the nucleic acid sequence of SEQ ID NO: 2 or a complement thereof, or (ii) 40 consecutive bases sequence of the nucleic acid sequence of SEQ ID NO: 2 or a complement thereof, wherein the 40 consecutive bases sequence is the nucleic acid sequence of SEQ ID NO: 1, the complement of SEQ ID NO: 2 is the nucleic acid sequence of SEQ ID NO: 4, and the complement of SEQ ID NO: 1 is the nucleic acid sequence of SEQ ID NO: 3, respectively. The aptamer of the present invention specifically binds to Influenza A H1N1 subtype virus, and the aptamer has at least one stem-loop structure.

Another aspect of the present invention is to provide a microfluidic chip for detecting the existence of Influenza A H1N1 subtype virus in a subject, comprising at least one aptemer of the present invention.

Another aspect of the present invention is to provide a method for detecting the existence of Influenza A H1N1 subtype virus in a subject, comprising: (1) contacting a sample from the subject with the aptamer of the present invention that specifically binds to the Influenza A H1N1 subtype virus; and (2) detecting the existence of Influenza A H1N1 subtype virus in the sample bound with the aptamer of step (1), if any; wherein the sample is laryngeal epithelial cells, sputum, or serum. The method further comprises conjugating the aptamer to a surface of a magnetic bead to form an aptamer-conjugated magnetic bead, wherein the Influenza A H1N1 subtype virus is captured by the aptamer-conjugated magnetic bead and a magnetic field is used to isolate the aptamer-conjugated magnetic bead bound with the Influenza A H1N1 subtype virus. The method of detecting the existence of Influenza A H1N1 subtype virus in the sample includes but does not limit to gel electrophoresis.

The Influenza A H1N1 subtype-specific aptamer of the present invention establishes high specificity and binding activity, thus is available for the detection of Influenza A H1N1 subtype virus. Apart from the fact that the molecular weight of the aptamer is low, the aptamer also can be stable in heat, resist degradation, be stored for a long period of time, be reusable, and easily attach to other molecules. In comparison with antibody, the aptamer can not only overcome the drawbacks caused by animal production but also increase the likelihood of amplification as well as reserve the accuracy of production.

The present invention is further explained in the following embodiment illustration and examples. Those examples below should not, however, be considered to limit the scope of the invention, it is contemplated that modifications will readily occur to those skilled in the art, which modifications will be within the spirit of the invention and scope of the appended claims.

DETAILED DESCRIPTION OF THE PREFERRED EMBODIMENT

Figure 1:
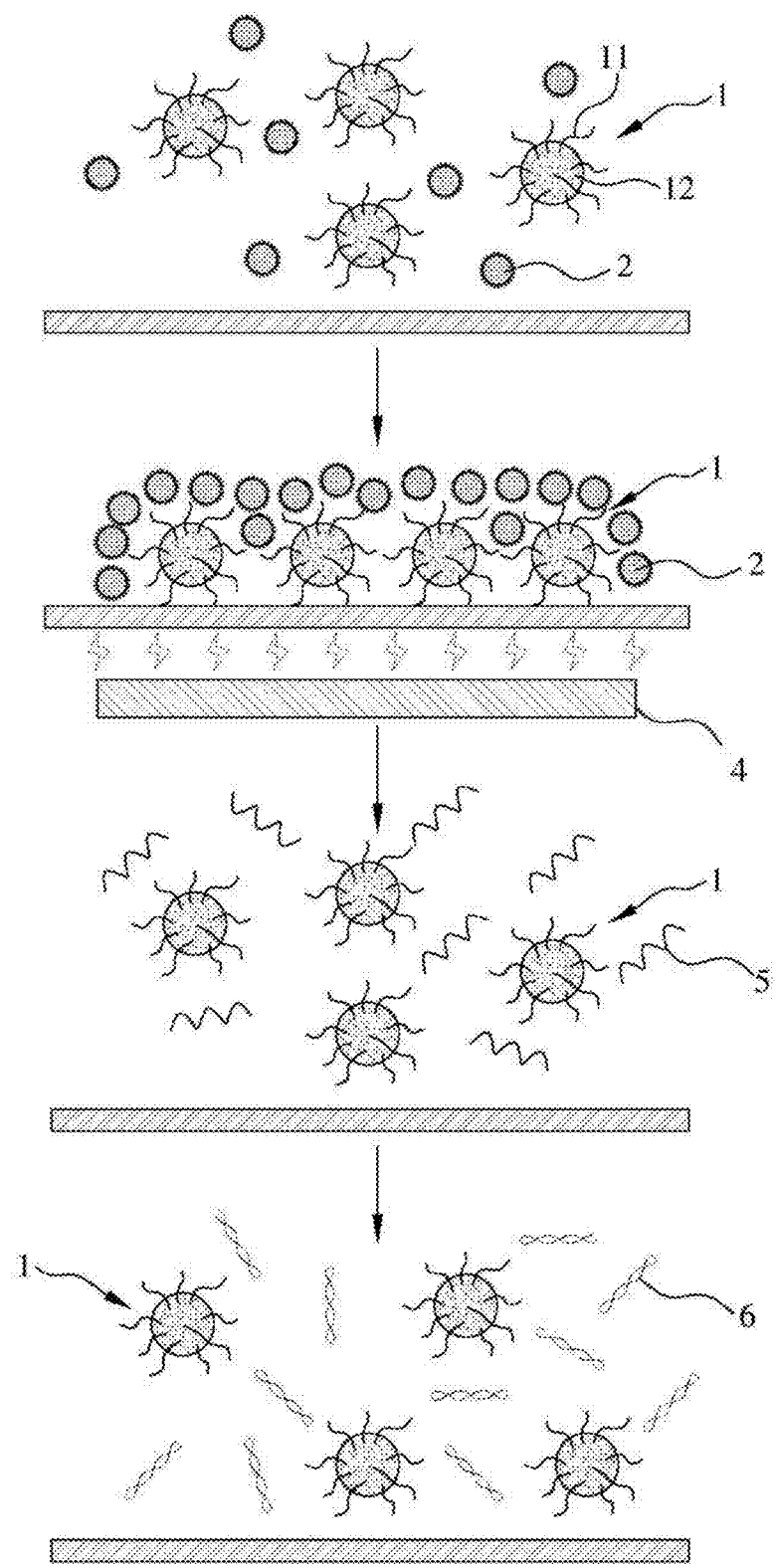
FIG. 1, flow chart for the selection of the target virus using the aptamer-conjugated magnetic beads of the present invention.

The present invention provides an aptamer with high specificity and binding activity for Influenza A H1N1 subtype virus, which was selected using the combination of systematic evolution of ligands by exponential enrichment (SELEX) and microfluidic chip technology. The aptamer of the present invention was further conjugated onto magnetic beads for binding reaction with various viruses to confirm its high specificity for Influenza A H1N1 subtype virus. On the other hand, both the aptamer of the present invention and antibody were conjugated onto magnetic beads and different concentrations of Influenza A H1N1 subtype virus were used for binding reaction to confirm the higher sensitivity of the aptamer comparing to the sensitivity of the antibody.

DEFINITION

As used herein, the terms "polynucleotide", "nucleic acid", "nucleic acid molecule", "nucleic acid sequence", "polynucleotide sequence", "nucleotide sequence", and "bases sequence" are interchangeable to refer to polymeric forms of nucleotides of any length. The polynucleotides can comprise deoxyribonucleotides, ribonucleotides, and/or their analogs or derivatives. Nucleotide sequences shown herein are listed in the 5' to 3' direction.

An aptamer is "specific for" Influenza A H1N1 subtype virus when the aptamer binds to or interact with Influenza A H1N1 subtype virus but does not bind to or interact significantly with other viruses or cells.

As used herein, the term "binding to", "binds to", or "bound to" refer to any of direct binding, indirect binding, covalent binding, or non-covalent binding, unless otherwise specifically indicated.

A "sample" is any biological sample derived from a subject, patient. The term includes, but is not limit to, biological fluids such as blood, serum, plasma, urine, cerebrospinal fluid, tears, saliva, laryngeal epithelial cells, sputum, lymph, dialysis fluid, lavage fluid, semen, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization; or enrichment for certain components, such as polynucleotides or polypeptides. Also included in the term are derivatives and fractions of patient samples. A patient sample may be used in a diagnostic or other monitoring assay.

As used herein, the terms "microfluidic device," "integrated microfluidic device," and "chip," are used interchangeably to refer to a single integral unit that has a microfluidic reactor, microfluidic flow channels, and valves. Microfluidic devices typically also have other microfluidic components, such as pumps, columns, mixers, and the like. Most often the chip is fabricated from elastomer, glass, or silicon. Typically, the chip is box-shaped with a height that is relatively small compared to length and width; however, the chip can have other shapes including cubical, cylindrical, and others.

Aptamers can be screened by any suitable methods in the art, for example, aptamers can be screened and identified from a random aptamer library by SELEX (systematic evolution of ligands by exponential enrichment). In certain preferred embodiments, aptamers that bind to a cell surface target molecule can be suitably screened and selected by a modified selection method herein referred to as cellSELEX or cellular-SELEX, even if the identity of the cell surface target molecule is unknown. In certain other preferred embodiments, aptamers that bind to a cell surface target molecule can be screened by capillary electrophoresis and enriched by SELEX based on the observation that aptamer-target molecule complexes exhibited retarded migration rate in native polyacrylamide gel electrophoresis as compared to unbound aptamers. The other making and use of aptamers are well known in the art. For example, U.S. Pat. No. 8,552,166 discloses High-affinity nucleic acid aptamers against sclerostin protein; U.S. Pat. No. 8,541,561 discloses DNA aptamer, the content of which are all incorporated herein by reference in their entireties. In addition, in certain other preferred embodiments, aptamers can also be synthesized by any suitable methods in the art, for instance, U.S. Pat. No. 8,569,252 discloses nucleolin specific aptamer and use thereof in which the aptamer can be synthesized using synthesizer, the content of which is also incorporated herein by reference in its entirety.

Material and Method

Single-Stand DNA Library (ssDNA Library)

The sequence of the ssDNA library contains: a randomized 40-mer nucleic acid sequence in the center flanked by 16-mer primers on both ends. One of the nucleic acid sequences included in the ssDNA library is shown as follow:

5'-GGCAGGAAGACAAACA-N₄₀-TGGTCTGTGGTGCTGT-3', wherein (SEQ ID NO: 5)
5'-GGCAGGA-AGACAAACA-3'

(SEQ ID NO: 5) is the Forward primer (F1);

(SEQ ID NO: 6)
5'-ACAGCACCACAGACCA-3'

(SEQ ID NO: 6) is the Reverse primer (R1). Another nucleic acid sequence included in the ssDNA library is shown as follow:

5'-ACAGCACCACAGACCA-N<sub>40</sub>-TGTTTGTCTTCCTGCC-3', wherein (SEQ ID NO: 7)
    5'-ACAGCACC-ACAGACCA-3'

(SEQ ID NO: 7) is the Forward primer (F2);

(SEQ ID NO: 8)
    5'-GGCAGGAAGACAAACA-3'

(SEQ ID NO: 8) is the Reverse primer (R2). The single-strand DNA selected from the ssDNA library via SELEX is termed the aptamer in the present invention when it is specific for one particular virus.

Preparation of Anti-Influenza Virus Nucleoprotein Monoclonal Antibodies Conjugated Magnetic Beads In order to capture different types of influenza virus, anti-influenza A virus nucleoprotein monoclonal antibodies (anti-NP-A mAb, H16L-10-4R5 cell line (HB-65), ATCC Co., USA) and anti-influenza B virus nucleoprotein monoclonal antibodies (anti-NP-B mAb, influenza B nucleoprotein (B017), GeneTex Co., USA) were utilized in the present invention. These anti-NP-A mAbs or anti-NP-B mAbs were conjugated onto Epoxy-coated magnetic beads (diameter of the beads=4.5 μm, Dynabeads® M-450 Epoxy, Invitrogen Co., USA) for the screen of Influenza A H1N1 subtype-specific aptamers during SELEX. The surface of the magnetic beads was coated with an epoxy amino group, thiol and hydroxyl functional groups, which were used to couple with the specific anti-NP-A mAbs or anti-NP-B mAbs. Please refer to U.S. Pat. No. 8,624,008 issued on 7 Jan. 2014 for details regarding the preparation procedure of anti-influenza virus nucleoprotein monoclonal antibody conjugated magnetic beads, and the content of which is incorporated herein by reference in its entirety.

Preparation of Influenza a H1N1 Subtype-Specific Aptamer-Conjugated Magnetic Beads Influenza A H1N1 subtype-specific aptamers were selected from ssDNA library using SELEX microfluidic chip. The aptamers were conjugated onto carboxylic acid coated magnetic beads (diameter of the beads=1 μm, Dynabeads® Myone™ Carboxylic Acid, Invitrogen Co., USA). The surfaces of the magnetic beads were coated with carboxylic groups which served as bifunctional cross-linkers and bond to amine groups. Please refer to U.S. Pat. No. 8,624,008 issued on 7 Jan. 2014 for details regarding the preparation procedure of Influenza A H1N1 subtype-specific aptamer-conjugated magnetic beads, and the content of which is incorporated herein by reference in its entirety.

Screening of Influenza a H1N1 Subtype-Specific Aptamer by the Use of SELEX Microfluidic Chip Positive selection and negative selection were both performed to obtain aptamers with high specificity for Influenza A H1N1 subtype viruses. Firstly, anti-NP-A mAb conjugated magnetic beads ($4 \times 10^8$ beads/mL) were used to recognize target virus, i.e. Influenza A virus. During this step, viruses were bond to the mAb-conjugated magnetic beads to form a virus-magnetic bead complex. The ssDNA library (10 μM of random single strand DNA sequences pool in 10 μL) was co-incubated with the virus-magnetic bead complexes in the incubation chamber of the SELEX microfluidic chip while mixing by a suction-type pneumatic micropump/micromixer. ssDNA with high specificity for Influenza A H1N1 virus, namely the Influenza A H1N1 subtype-specific aptamer, could be captured by the virus-magnetic bead complex. This process was regard as positive selection. A magnetic field was applied at the bottom of the incubation chamber to collect those magnetic beads and a phosphate buffered saline (1×PBS, pH=7.4) buffer was used to wash away unbound ssDNA sequences. Then, the ssDNA sequences captured were moved to the PCR chamber for amplification via micropump.

As for negative selection, ssDNA library was co-incubated with both Influenza B viruses and anti-NP-B mAb conjugated magnetic beads. Magnetic field was applied to capture the magnetic beads after incubation. The supernatant containing unbound ssDNA was collected and moved to the PCR chamber for amplification.

The above PCR reaction was controlled by a temperature control module equipped with a thermoelectric cooler which is set beneath the microfluidic chip. The PCR reaction started at 95° C. for 10 minutes for DNA denaturation, then, the process comprising denaturation at 95° C. for 30 seconds, annealing at 68° C. for 30 seconds and extension at 72° C. for 30 seconds was continued for 20 cycles. After the 20 cycles, PCR reaction was completed with a final extension step at 72° C. for 10 min and the products were stored at 4° C.

In sum, the SELEX microfluidic chip includes: a suction-type pneumatic micropump/micromixer as control module, a chamber for reagent and sample, a PCR module, and a module for the separation of magenetic beads and aptamers. After 5 cycles of positive and negative selection, the aptamer with high specificity and high binding activity to Influenza A H1N1 subtype virus can be obtained.

TA-Cloning of Influenza a H1N1 Subtype-Specific Aptamer

Aptamers selected and amplified by the above SELEX microfluidic chip were further cloned using TOPO Vector® system (pCR® 2.1-TOPO®, 3.9 kb, Invitrogen Co., USA). A total of 28 aptamers (single strand DNA) were cloned and were further isolated and purified using a commercial kit (Favor Prep™ Plasmid DNA Extraction Mini Kit, Favorgen Biotech Co., Taiwan).

One of the cloned DNA was selected and both its sense strand and antisense strand were sequenced. The sense strand sequence of the DNA is:

(SEQ ID NO: 4)
5'-ACAGCACCACAGACCACCCGCGGATGCCGGTCCCTACGCGTCGCTGT

CACGCTGGCTGTTTGTCTTCCTGCC-3';

(SEQ ID NO: 4); the antisense strand sequence of the DNA is:

(SEQ ID NO: 2)
5'-GGCAGGAAGACAAACAGCCAGCGTGACAGCGACGCGTAGGGACCGG

CATCCGCGGGTGGTCTGTGGTGCTGT-3'.

(SEQ ID NO: 2). The antisense strand sequence above contains the DNA sequence specific for Influenza A H1N1 subtype viruses, which is:

(SEQ ID NO: 1)
5'-GCCAGCGTGACAGCGACGCGTAGGGACCGGCATCCGCGGG-3';

GG-3' (SEQ ID NO: 1); the sense strand sequence above contains the DNA sequence specific for Influenza A H1N1 subtype viruses, which is:

(SEQ ID NO: 3)
5'-CCCGCGGATGCCGGTCCCTACGCGTCGCTGTCACGCTGGC-3'.

(SEQ ID NO: 3).

Example 1

Detection of Target Virus Using Influenza a H1N1 Subtype-Specific Aptamer-Conjugated Magnetic Beads Please refer to FIG. 1, firstly, Influenza A H1N1 subtype-specific aptamer 11 and magnetic beads 12 were combined to form the Influenza A H1N1 subtype specific aptamer-conjugated magnetic beads 1, the aptamer-conjugated magnetic beads were then mixed with target viruses 2. The Influenza A H1N1 subtype-specific aptamer 11 is the abovementioned sense strand DNA sequence (SEQ ID NO: 4) and antisense strand DNA sequence (SEQ ID NO: 2), whereas the target viruses 2 are: Influenza A H1 subtype virus (InfA/H1), Influenza B virus (InfB), or Influenza A H3 subtype virus (InfA/H3). After mixing, magnetic field 4 was applied to collect magnetic beads on a substrate 3. After eluting for three times, target viruses that bond to the Influenza A H1N1 subtype-specific aptamers were reserved. Then, the viruses captured were broken down at 95° C. to release the RNA 5 of the target virus. Reverse transcription polymer chain reaction (RT-PCR) was used to amplify the DNA 6 of the target virus. Finally, gel electrophoresis was performed using the amplified cDNA of the target viruses.

Figure 2:
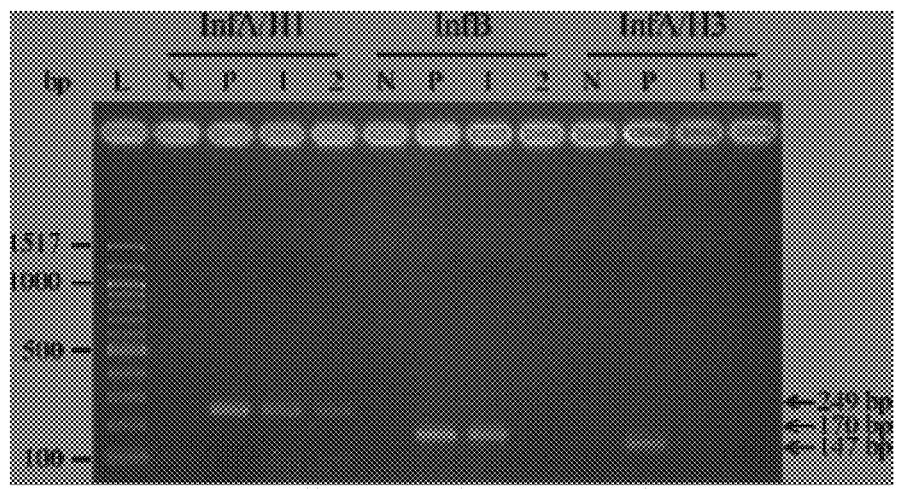
FIG. 2, comparison of the sensitivities of the sense and anti-sense strand of the aptamer of the present invention.

As shown in FIG. 2, lane 1 refers to the DNA sequence of the Influenza A H1N1 subtype-specific aptamer (SEQ ID NO: 4), lane 2 refers to the DNA sequence of the Influenza A H1N1 subtype-specific aptamer (SEQ ID NO: 2), lane N refers to double-distilled water that serves as negative control, lane P refers to the RNA of the target virus that serves as positive control, and lane L refers to the DNA ladder of 100 base pair (bp). After amplification, the length of the gene fragments of the target viruses, namely InfA/H1, InfB, and InfA/H3, are 249 bp, 170 bp, and 147 bp, respectively. According to FIG. 2, the DNA sequence of the Influenza A H1N1 subtype-specific aptamer (SEQ ID NO: 2) only shows band in InfA/H1 but not in either InfB or InfA/H3, indicating its high specificity for Influenza A H1N1 subtype virus; on the other hand, the DNA sequence of the Influenza A H1N1 subtype-specific aptamer (SEQ ID NO: 4), although, can bind with InfA/H1, it can also bind with InfB (band appears on lane 1 of InfB), indicating that its specificity for Influenza A H1N1 subtype virus is comparatively lower.

Figure 3:
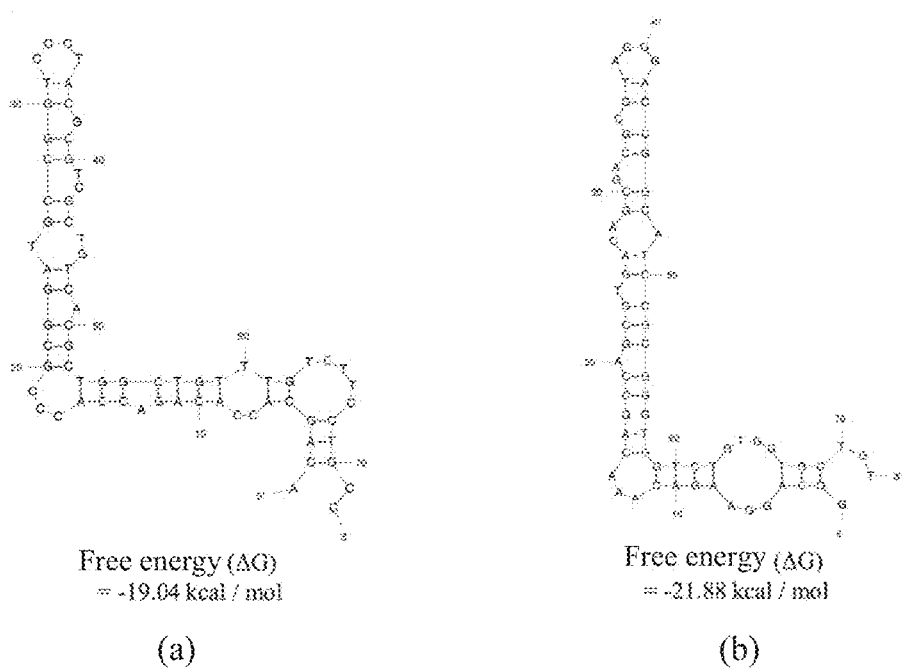
FIG. 3, illustration of the secondary structure of the aptamer of the present invention: (a) the secondary structure of the nucleic acid sequence of SEQ ID NO: 4; (b) the secondary structure of the nucleic acid sequence of SEQ ID NO: 2.

The secondary structure of the antisense strand DNA sequence of Influenza A H1N1 subtype-specific aptamer (SEQ ID NO: 2) and the sense strand DNA sequence of Influenza A H1N1 subtype-specific aptamer (SEQ ID NO: 4) were further predicted using MFOLD software and the results were shown in FIG. 3. According to the results of prediction, the secondary structure of the sense strand DNA sequence of Influenza A H1N1 subtype-specific aptamer (SEQ ID NO: 4) (FIG. 3($a$)) establishes free energy of −19.04 kcal/mol, while the secondary structure of the antisense strand DNA sequence of Influenza A H1N1 subtype-specific aptamer (SEQ ID NO: 2) (FIG. 3($b$)) establishes free energy of −21.88 kcal/mol. In conclusion, the antisense strand DNA sequence of Influenza A H1N1 subtype-specific aptamer (SEQ ID NO: 2) is more specific and stable comparing to the sense strand DNA sequence of Influenza A H1N1 subtype-specific aptamer (SEQ ID NO: 4).

Free energy ($\Delta G$) is a thermodynamic property that predicts whether a reversible process will occur spontaneously at constant temperature and pressure. Thus, the quantity of $\Delta G$ (measured in kcal/mol) is negative for spontaneous or energy-releasing processes, and is positive for non-spontaneous or energy-consuming reactions. The secondary structures of the Influenza A H1N1 subtype-specific aptamers establish negative free energy indicating that the reaction of forming the secondary structure of the aptamer is a spontaneous energy-releasing process. In addition, the lower the free energy the more stable the aptamer would be, thus, the aptamer of the present invention can substitute for conventional antibody as the biomarker for the detection of Influenza A H1N1 subtype virus.

Example 2

Specificity Test Using Influenza a H1N1 Subtype-Specific Aptamer-Conjugated Magnetic Beads Influenza A H1N1 subtype-specific aptamer-conjugated magnetic beads were co-incubated with various viruses including Influenza A H1N1 subtype virus, Influenza B virus, Influenza A H3N2 subtype virus, Dengue virus-2, and Enterovirus-71. Human chromosomal DNA was also used. Commercially available reagents were used to extract the RNA of various viruses as well as the DNA of human chromosome for RT-PCR.

In the present embodiment, deactivated Influenza A H1N1 subtype virus and deactivated Influenza B virus were used and their initial titer were 64 HAU and 128 HAU, respectively. In addition, Influenza A H3N2 subtype virus, Dengue virus-2, and Enterovirus-71 were used and their initial titer were 100 HAU, $5\times10^6$ PFU, and $2\times10^7$ PFU, respectively. The viruses were first mixed in serum and then were added to near-confluent (90%) monolayers of Madin-Darby canine kidney (MDCK) cells. The viruses and MDCK cells were incubated at 35° C. with 5% $CO_2$. The virus/serum mixture was then replaced with a serum-free medium supplemented with 0.05% Trypsin-EDTA (Invitrogen Co., USA) and the cells were incubated at 35° C. with 5% $CO_2$. After harvesting the supernatant from the culture medium, the virus particles were collected from the medium supernatant and froze at −80° C. until used.

RT-PCR primers were individually designed for the above viruses and the human chromosomal DNA. The length of amplified gene fragments for each viruses and human chromosomal DNA are listed as follow: Influenza A H1N1 subtype virus (249 bp), Influenza B virus (170 bp), Influenza A H3N2 virus (143 bp), Dengue virus-2 (248 bp), Enterovirus-71 (232 bp), and Human chromosomal DNA (225 bp). Please see Table 1 for the PCR primers used in the present embodiment.

TABLE 1

PCR primers for various viruses

| Virus | Primer | Sequence(5'→3') | Annealing temperature | Average amplification size(bp) |
|---|---|---|---|---|
| Influenza A H1N1 subtype | Forward | GTGTTCATCACCCGCC (SEQ ID NO: 9) | 58° C. | 249 |
| | Reverse | AGCCTCTACTCAGTGC (SEQ ID NO: 10) | | |
| Influenza A H3N2 subtype | Forward | AATGCATCACTCCAAATGG (SEQ ID NO: 11) | 56° C. | 147 |
| | Reverse | TAGTTTGTTTCTCTGGTAC (SEQ ID NO: 12) | | |
| Influenza B | Forward | AAATACGGTGGATTAAATAAAAGCAA (SEQ ID NO: 13) | 56° C. | 170 |
| | Reverse | CCAGCAATAGCTCCGAAGAAA (SEQ ID NO: 14) | | |
| Dengue virus-2 | Forward | GAGTGGAGTGGGAAGGAGAAGGG (SEQ ID NO: 15) | 58° C. | 248 |
| | Reverse | CTTCTTGGTGTTGGTCTTTGC (SEQ ID NO: 16) | | |
| Enterovirus (EV-71) | Forward | AGTATGATTGAGACTCGGTG (SEQ ID NO: 17) | 58° C. | 232 |
| | Reverse | GCGACAAAAGTGAACTCTGC (SEQ ID NO: 18) | | |
| Human chromosomal DNA | Forward | CCATGGAGAAGGCTGGGG (SEQ ID NO: 19) | 60° C. | 225 |
| | Reverse | CAAAGTTGTCATGGATGACC (SEQ ID NO: 20) | | |

The result of RT-PCR was shown using 2% agarose gel stained with ethidium bromide (EtBr).

Figure 4:
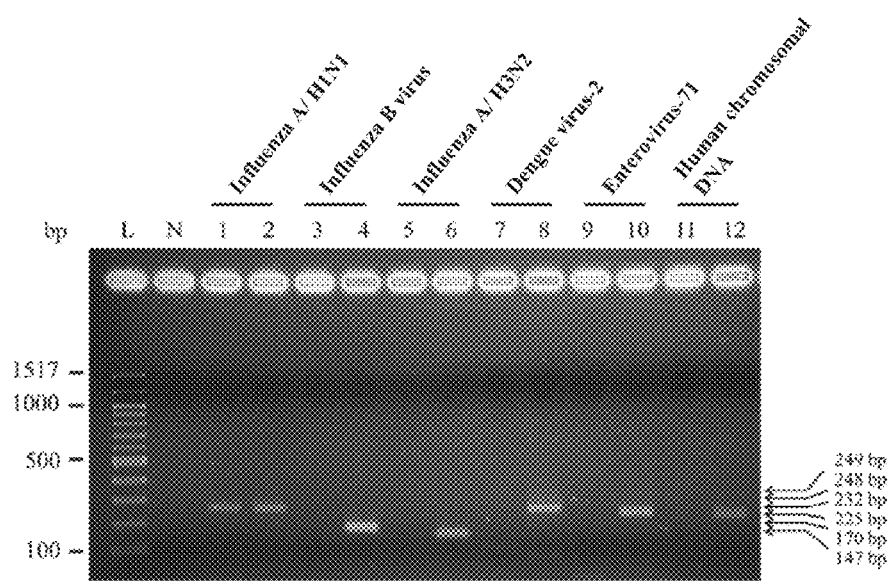
FIG. 4, gel electrophoresis of the specificity by using the aptamer-conjugated magnetic beads of the present invention for the detection of various viruses.

As shown in FIG. 4, the gel electrophoresis of the specificity by using Influenza A H1N1 subtype-specific aptamer (SEQ ID NO: 2) conjugated magnetic beads for the detection of various viruses. The Experimental groups using the above aptamer-conjugated magnetic beads are shown as the following lanes: lane 1, 3, 5, 7, 9, and 11; the Control groups containing viral RNA of InfA/H1, InfB, InfA/H3, DENV-2, EV-71, and human chromosomal DNA are shown as the following lanes: lane 2, 4, 6, 8, 10, and 12, respectively. There were bands appeared on lanes of both the Experiment and Control groups of Influenza A H1N1 subtype virus (lane 1 and 2) indicating that the aptamer of the present invention can bind with Influenza A H1N1 subtype virus. On the other hand, only lanes of the Control groups of other viruses and human chromosomal DNA (lane 4, 6, 8, 10, and 12) showed bands indicating that the aptamer of the present invention does not bind with other viruses and human chromosomal DNA. Thus, the high specificity of the Influenza A H1N1 subtype-specific aptamer of the present invention was confirmed.

Example 3

Sensitivity Test Using Influenza a H1N1 Subtype-Specific Aptamer-Conjugated Magnetic Beads The sensitivity of the aptamer of the present invention and anti-influenza virus nucleoprotein monoclonal antibodies were compared. The initial concentration of the test Influenza A virus was 64 HAU and was gradually diluted with 10-fold dilution to $64 \times 10^{-5}$ HAU.

Figure 5:
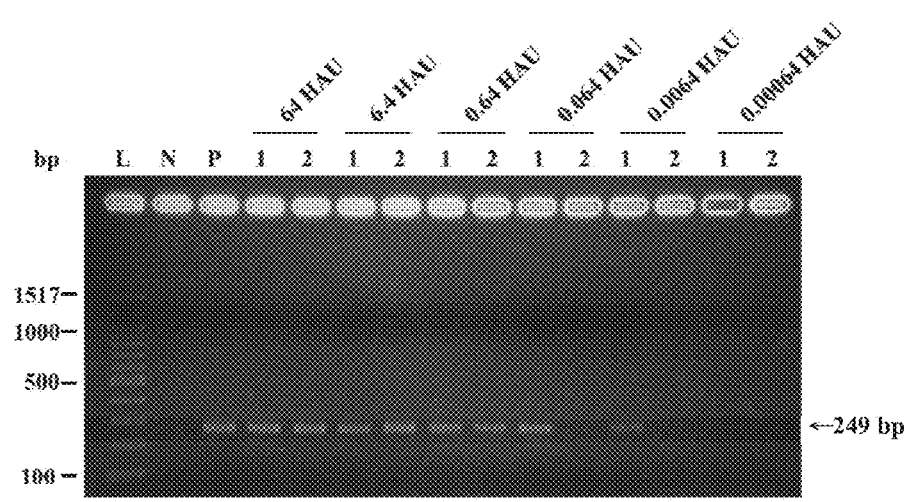
FIG. 5, gel electrophoresis of the sensitivity by using the aptamer-conjugated magnetic beads of the present invention for the detection of different concentrations of H1N1 influenza virus.

FIG. 5 shows the gel electrophoresis of the sensitivity by using Influenza A H1N1 subtype-specific aptamer (SEQ ID NO: 2) conjugated magnetic beads for the detection of different concentrations of H1N1 influenza virus. The length of the fragment of Influenza A H1N1 subtype viral DNA is 249 bp. Lane L refers to the DNA ladder of 100 bp, in which double-distilled water was used for RT-PCR; lane P refers to the control group, in which Influenza A H1N1 subtype viral RNA was used for RT-PCR. Lane 1 of each different concentration refers to the Influenza A H1N1 subtype-specific aptamer-conjugated magnetic beads; while lane 2 of each concentration refers to the anti-NP A mAb conjugated magnetic beads. Only one band is visible on the lanes of $64 \times 10^{-3}$ HAU and $64 \times 10^{-4}$ HAU, indicating that only the Influenza A H1N1 subtype-specific aptamer-conjugated magnetic beads can bind with Influenza A H1N1 subtype virus; thus, the sensitivity of Influenza A H1N1 subtype-specific aptamer of the present invention is confirm to be 100 times higher than the sensitivity of anti-NP A mAb.

Example 4

Detection of Virus in Sample Using Influenza a H1N1 Subtype-Specific Aptamer

To examine the clinical feasibility of the Influenza A H1N1 subtype-specific aptamer of the present invention, $6.4 \times 10^{1}$ HAU of Influenza A H1N1 subtype virus and Influenza B virus were mixed with sample, wherein the sample were laryngeal epithelial cells, sputum, and serum. The sample containing viruses were co-incubated with the Influenza A H1N1 subtype-specific aptamer-conjugated magnetic beads and were then subjected to PCR.

Figure 6:
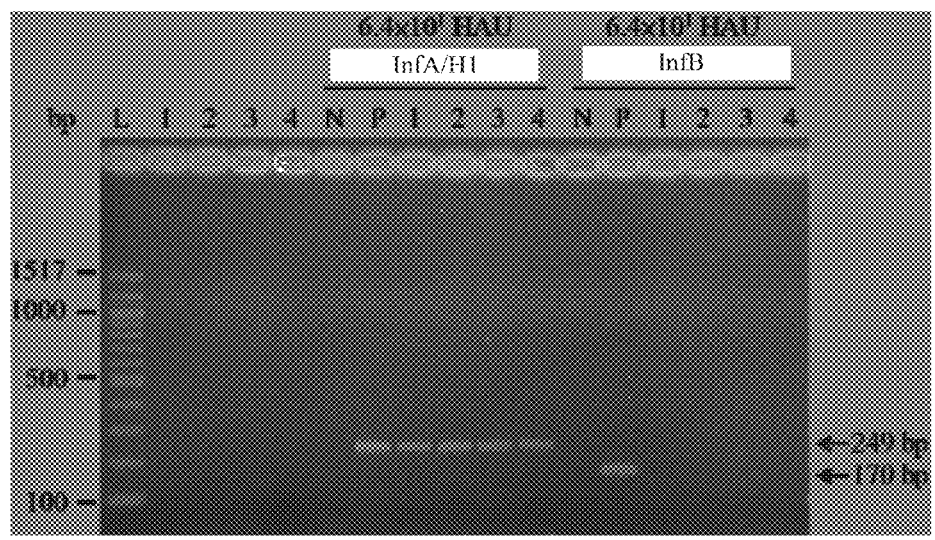
FIG. 6, gel electrophoresis of the aptamer-conjugated magnetic beads of the present invention for the detection of H1N1 influenza virus in the sample.

In FIG. 6, the length of viral DNA fragment of Influenza A H1N1 subtype virus and Influenza B virus are 249 bp and 170 bp, respectively. Lane L refers to the DNA ladder of 100 bp; lane N refers to double-distilled water which serves as control group; lane P refers to the control group, in which the RNA of Influenza A H1N1 subtype virus/Influenza B are used in RT-PCR. Among the lanes of each given virus, lane 1 refers to the sample of mixing the given virus with 1×PBS buffer, lane 2 refers to the laryngeal epithelial cells sample containing the given virus, lane 3 refers to the sputum sample containing the given virus, and lane 4 refers to the serum sample containing the given virus. According to FIG. 6, bands are clearly visible in lanes where the Influenza A H1N1 subtype-specific aptamer-conjugated magnetic beads of the present invention and each sample containing Influenza A H1N1 subtype virus were co-incubated. On the other hand, no bands can be seen in lanes where the Influenza A H1N1 subtype-specific aptamer-conjugated magnetic beads of the present invention and each sample containing Influenza B virus were co-incubated. The result indicates that Influenza A H1N1 subtype-specific aptamer of the present invention still establish high specificity upon detecting virus in sample such as sputum, serum, etc. Hence, the present invention can accurately detect Influenza A H1N1 subtype virus in sample and can be used effectively as the biomarker for the detection of Influenza A H1N1 subtype virus.

In conclusion, the Influenza A H1N1 subtype-specific aptamer of the present invention establishes high specificity and high binding activity. The aptamer has low molecular weight and can be easily changed or doubled. The aptamer also has advantages such as reusable and easily to be attached to other molecules; hence, when comparing to antibody, the aptamer can not only overcome the drawbacks caused by animal production but also increase the likelihood of amplification as well as reserve the accuracy of production. Moreover, the aptamer is also heat-stable and can resist degradation, thus, become possible regarding long-term storage.

What is claimed is:

1. An aptamer comprising (i) the nucleic acid sequence of SEQ ID NO: 2 or a complement thereof, or (ii) 40 consecutive bases sequence of the nucleic acid sequence of SEQ ID NO: 2 or a complement thereof, wherein the 40 consecutive bases sequence is the nucleic acid sequence of SEQ ID NO: 1 and the aptamer specifically binds to Influenza A H1N1 subtype virus.

2. The aptamer according to claim 1, wherein the aptamer has at least one stem-loop structure.

3. The aptamer according to claim 1, wherein the complement of SEQ ID NO: 2 is the nucleic acid sequence of SEQ ID NO: 4.

4. The aptamer according to claim 1, wherein the complement of SEQ ID NO: 1 is the nucleic acid sequence of SEQ ID NO: 3.

5. The aptamer according to claim 3, wherein the aptamer contains has at least one stem-loop structure.

6. A microfluidic chip for detecting the existence of Influenza A H1N1 subtype virus in a subject, comprising at least one aptemer according to claim 1.

7. A method for detecting the existence of Influenza A H1N1 subtype virus in a subject, comprising:

(1) contacting a sample from the subject with the aptamer according to claim 1 that specifically binds to the Influenza A H1N1 subtype virus; and (2) detecting the existence of Influenza A H1N1 subtype virus in the sample bound with the aptamer of step (1), if any.

8. The method according to claim 7, wherein the sample is laryngeal epithelial cells, sputum, or serum.

9. The method according to claim 7, further comprising conjugating the aptamer to a surface of a magnetic bead to form an aptamer-conjugated magnetic bead.

10. The method according to claim 9, wherein the Influenza A H1N1 subtype virus is captured by the aptamer-conjugated magnetic bead and a magnetic field is used to isolate the aptamer-conjugated magnetic bead bound with the Influenza A H1N1 subtype virus.

* * * * *

SEQUENCE LISTING

```
<160> NUMBER OF SEQ ID NOS: 20

<210> SEQ ID NO 1
<211> LENGTH: 40
<212> TYPE: DNA
<213> ORGANISM: Artificial sequence
<220> FEATURE:
<223> OTHER INFORMATION: Synthetic nucleotide

<400> SEQUENCE: 1
gccagcgtga cagcgacgcg tagggaccgg catccgcggg                        40

<210> SEQ ID NO 2
<211> LENGTH: 72
<212> TYPE: DNA
<213> ORGANISM: Artificial sequence
<220> FEATURE:
<223> OTHER INFORMATION: Synthetic nucleotide

<400> SEQUENCE: 2
ggcaggaaga caaacagcca gcgtgacagc gacgcgtagg gaccggcatc cgcgggtggt    60
ctgtggtgct gt                                                       72

<210> SEQ ID NO 3
<211> LENGTH: 40
<212> TYPE: DNA
<213> ORGANISM: Artificial sequence
<220> FEATURE:
<223> OTHER INFORMATION: Synthetic nucleotide

<400> SEQUENCE: 3
cccgcggatg ccggtcccta cgcgtcgctg tcacgctggc                        40

<210> SEQ ID NO 4
<211> LENGTH: 72
<212> TYPE: DNA
<213> ORGANISM: Artificial sequence
<220> FEATURE:
<223> OTHER INFORMATION: Synthetic nucleotide

<400> SEQUENCE: 4
acagcaccac agaccacccg cggatgccgg tccctacgcg tcgctgtcac gctggctgtt    60
```

```
tgtcttcctg cc                                                              72

<210> SEQ ID NO 5
<211> LENGTH: 16
<212> TYPE: DNA
<213> ORGANISM: Artificial sequence
<220> FEATURE:
<223> OTHER INFORMATION: Synthetic primer

<400> SEQUENCE: 5
ggcaggaaga caaaca                                                          16

<210> SEQ ID NO 6
<211> LENGTH: 16
<212> TYPE: DNA
<213> ORGANISM: Artificial sequence
<220> FEATURE:
<223> OTHER INFORMATION: Synthetic primer

<400> SEQUENCE: 6
acagcaccac agacca                                                          16

<210> SEQ ID NO 7
<211> LENGTH: 16
<212> TYPE: DNA
<213> ORGANISM: Artificial sequence
<220> FEATURE:
<223> OTHER INFORMATION: Synthetic primer

<400> SEQUENCE: 7
acagcaccac agacca                                                          16

<210> SEQ ID NO 8
<211> LENGTH: 16
<212> TYPE: DNA
<213> ORGANISM: Artificial sequence
<220> FEATURE:
<223> OTHER INFORMATION: Synthetic primer

<400> SEQUENCE: 8
ggcaggaaga caaaca                                                          16

<210> SEQ ID NO 9
<211> LENGTH: 16
<212> TYPE: DNA
<213> ORGANISM: Artificial sequence
<220> FEATURE:
<223> OTHER INFORMATION: Synthetic primer

<400> SEQUENCE: 9
gtgttcatca cccgcc                                                          16

<210> SEQ ID NO 10
<211> LENGTH: 16
<212> TYPE: DNA
<213> ORGANISM: Artificial sequence
<220> FEATURE:
<223> OTHER INFORMATION: Synthetic primer

<400> SEQUENCE: 10
agcctctact cagtgc                                                          16

<210> SEQ ID NO 11
<211> LENGTH: 19
<212> TYPE: DNA
```

```
<213> ORGANISM: Artificial sequence
<220> FEATURE:
<223> OTHER INFORMATION: Synthetic primer

<400> SEQUENCE: 11
aatgcatcac tccaaatgg                                                    19

<210> SEQ ID NO 12
<211> LENGTH: 19
<212> TYPE: DNA
<213> ORGANISM: Artificial sequence
<220> FEATURE:
<223> OTHER INFORMATION: Synthetic primer

<400> SEQUENCE: 12
tagtttgttt ctctggtac                                                    19

<210> SEQ ID NO 13
<211> LENGTH: 26
<212> TYPE: DNA
<213> ORGANISM: Artificial sequence
<220> FEATURE:
<223> OTHER INFORMATION: Synthetic primer

<400> SEQUENCE: 13
aaatacggtg gattaaataa aagcaa                                            26

<210> SEQ ID NO 14
<211> LENGTH: 21
<212> TYPE: DNA
<213> ORGANISM: Artificial sequence
<220> FEATURE:
<223> OTHER INFORMATION: Synthetic primer

<400> SEQUENCE: 14
ccagcaatag ctccgaagaa a                                                 21

<210> SEQ ID NO 15
<211> LENGTH: 23
<212> TYPE: DNA
<213> ORGANISM: Artificial sequence
<220> FEATURE:
<223> OTHER INFORMATION: Synthetic primer

<400> SEQUENCE: 15
gagtggagtg ggaaggagaa ggg                                               23

<210> SEQ ID NO 16
<211> LENGTH: 21
<212> TYPE: DNA
<213> ORGANISM: Artificial sequence
<220> FEATURE:
<223> OTHER INFORMATION: Synthetic primer

<400> SEQUENCE: 16
cttcttggtg ttggtctttg c                                                 21

<210> SEQ ID NO 17
<211> LENGTH: 20
<212> TYPE: DNA
<213> ORGANISM: Artificial sequence
<220> FEATURE:
<223> OTHER INFORMATION: Synthetic primer

<400> SEQUENCE: 17
agtatgattg agactcggtg                                                   20
```

-continued

```
<210> SEQ ID NO 18
<211> LENGTH: 20
<212> TYPE: DNA
<213> ORGANISM: Artificial sequence
<220> FEATURE:
<223> OTHER INFORMATION: Synthetic primer

<400> SEQUENCE: 18
gcgacaaaag tgaactctgc                                            20

<210> SEQ ID NO 19
<211> LENGTH: 18
<212> TYPE: DNA
<213> ORGANISM: Artificial sequence
<220> FEATURE:
<223> OTHER INFORMATION: Synthetic primer

<400> SEQUENCE: 19
ccatggagaa ggctgggg                                              18

<210> SEQ ID NO 20
<211> LENGTH: 20
<212> TYPE: DNA
<213> ORGANISM: Artificial sequence
<220> FEATURE:
<223> OTHER INFORMATION: Synthetic primer

<400> SEQUENCE: 20
caaagttgtc atggatgacc                                            20
```